United States Patent
Rahe

[11] Patent Number: 5,312,379
[45] Date of Patent: May 17, 1994

[54] DEVICE FOR COLLECTING UNCONTROLLABLY RELEASED URINE

[76] Inventor: Martin Rahe, Drosselweg 67, D04971 Hullhorst, Fed. Rep. of Germany

[21] Appl. No.: 671,854
[22] PCT Filed: Oct. 11, 1989
[86] PCT No.: PCT/DE89/00648
§ 371 Date: Apr. 11, 1991
§ 102(e) Date: Apr. 11, 1991
[87] PCT Pub. No.: WO90/03771
PCT Pub. Date: Apr. 19, 1990

[30] Foreign Application Priority Data
Oct. 12, 1988 [DE] Fed. Rep. of Germany ....... 3834725
Sep. 22, 1989 [DE] Fed. Rep. of Germany ....... 3931659

[51] Int. Cl.⁵ .................................................. A61M 1/00
[52] U.S. Cl. ................................. 604/318; 604/327; 128/771
[58] Field of Search ............... 604/317, 318, 322, 377, 604/346, 388, 356, 403, 404; 128/760, 767, 771, 667; 73/863.73; 424/3, 7.1

[56] References Cited

U.S. PATENT DOCUMENTS

| | | | |
|---|---|---|---|
| 3,640,388 | 2/1972 | Ferrari . | |
| 3,660,033 | 5/1972 | Schwartz . | |
| 3,918,433 | 11/1975 | Fuisz | 128/771 |
| 4,661,100 | 4/1987 | Rechsteiner | 604/318 |
| 4,753,299 | 6/1988 | Nuller | 128/771 |
| 4,827,944 | 5/1989 | Nugent | 604/318 |
| 4,872,868 | 10/1989 | Chevallier | 128/771 |
| 4,957,108 | 9/1990 | Schoendorfer et al. | 128/771 |
| 5,119,830 | 6/1992 | Davis | 128/771 |
| 5,137,031 | 8/1992 | Guirguis | 128/771 |

FOREIGN PATENT DOCUMENTS

| | | |
|---|---|---|
| 0146691 | 7/1985 | European Pat. Off. . |
| 3504527 | 2/1986 | Fed. Rep. of Germany . |
| 1-263557 | 10/1989 | Japan ................................ 128/771 |

Primary Examiner—Randall L. Green
Assistant Examiner—K. M. Reichie
Attorney, Agent, or Firm—Sprung Horn Kramer & Woods

[57] ABSTRACT

A device (1) for collecting uncontrollably released urine including an introducing tube (2) passing a transparent collecting device. The invention proposes checking the collected urine as to impending and existing germinal infections by providing indicators (10) that are applied to a urine-exposed side of a control card (9, 9', 9'', 9''') attached inside the collecting device (3), and covering the control card (9 to 9''') on its urine-exposed side with a membrane (17) that slows down the reception of urine, on the one hand, and works against the indicators being washed out, on the other hand. The indicators (10) of the control card (9, 9', 9'', 9''') are protected from indication errors due to the slow passage of urine through the membrane (17).

8 Claims, 2 Drawing Sheets

DEVICE FOR COLLECTING UNCONTROLLABLY RELEASED URINE

BACKGROUND OF THE INVENTION

The present invention relates to a device for collecting uncontrollably released urine passing through an introducing tube into a transparent collecting device.

Users of the stated device often suffer from infectious diseases that can attack the efferent urinary passages as well as the bladder and kidneys. To counteract these infections it is known to administer antiphlogistic drugs. However, these drugs lose their efficacy after being taken for some time. Orally applied drugs are also known that acidify the urine and thus slow down the increase of germs. Both drugs have undesirable side effects that make it necessary to discontinue their application. Furthermore, the wearer is supposed to change the device every day and go for a medical examination every two weeks.

SUMMARY OF THE INVENTION

The present invention is based on the problem of providing a device of the above-mentioned type that permits the quality of the urine to be signaled so that suitable measures can be taken in time to avoid an infection or so that a doctor can be consulted in the initial stage thereof.

This problem is solved by checking the collected urine as to impending and existing germinal infections by providing indicators that are applied to a urine exposed of a control card attached inside the collecting bag, and by covering the control card on its urine-exposed side with a membrane that slows down the reception of urine, on the one hand, and works against indicator substances being washed out, on the other hand.

Any currently used device of the above-mentioned type can be provided With the control card on the inside by adhesion or welding before the collecting bag is bonded. The membrane protects the indicators from indication errors, on the one hand, since it slows down the entrance of urine. The indicators show neither the excessive concentration of germs in the first urine nor the typical deviations in the residual urine, but rather the values integrated over the entire urine content. Since the membrane also protects the indicators from being washed out, the indication values can still be read unfalsified after many hours.

With the further features described hereinafter one obtains altogether a device whose indicators permit a precise indication of measured values.

The invention will be described in more detail below with reference to embodiment examples shown in the drawings.

DESCRIPTION OF THE PREFERRED EMBODIMENTS

Figure 1:
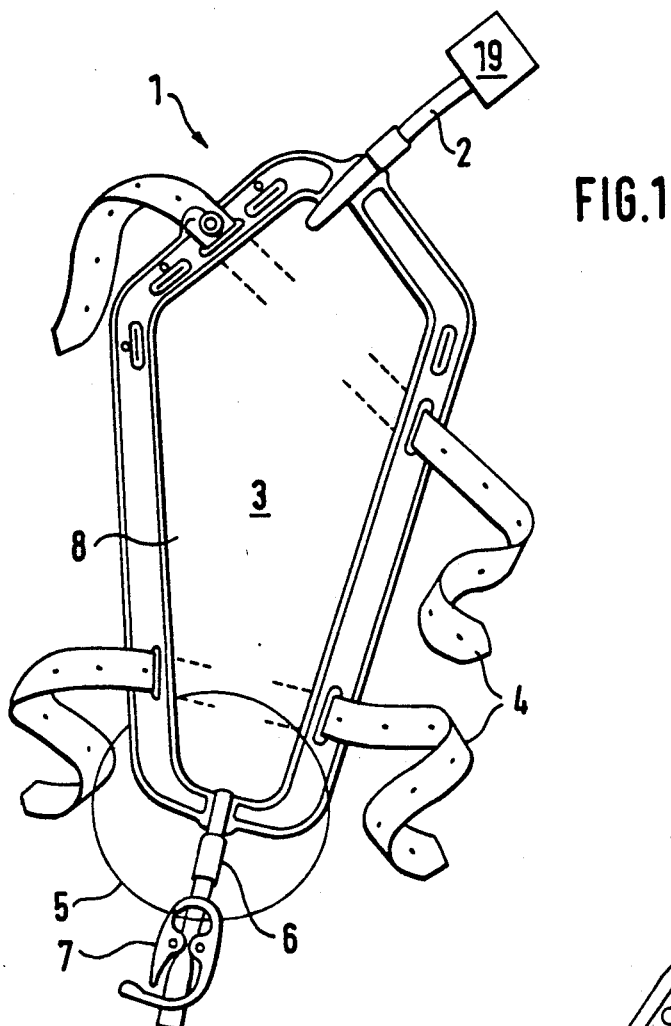
FIG. 1 shows a known device for collecting uncontrollably released urine passing through an introducing tube into a transparent, emptyable collecting bag provided with attachment straps.

FIG. 1 shows a device, referred to altogether as I, for collecting uncontrollably released urine flowing via an adapter 19 connected with the body and through an introducing tube 2 into a collecting bag 3. Collecting bag 3 with two attachment straps 4 is worn on the leg and is provided at its lower tapering end 5 with a short discharge tube 6 that is clamped shut by a clamp 7 through neutralizable spring force. All objects 1 to 6 are made of flexible transparent material.

Figure 2:
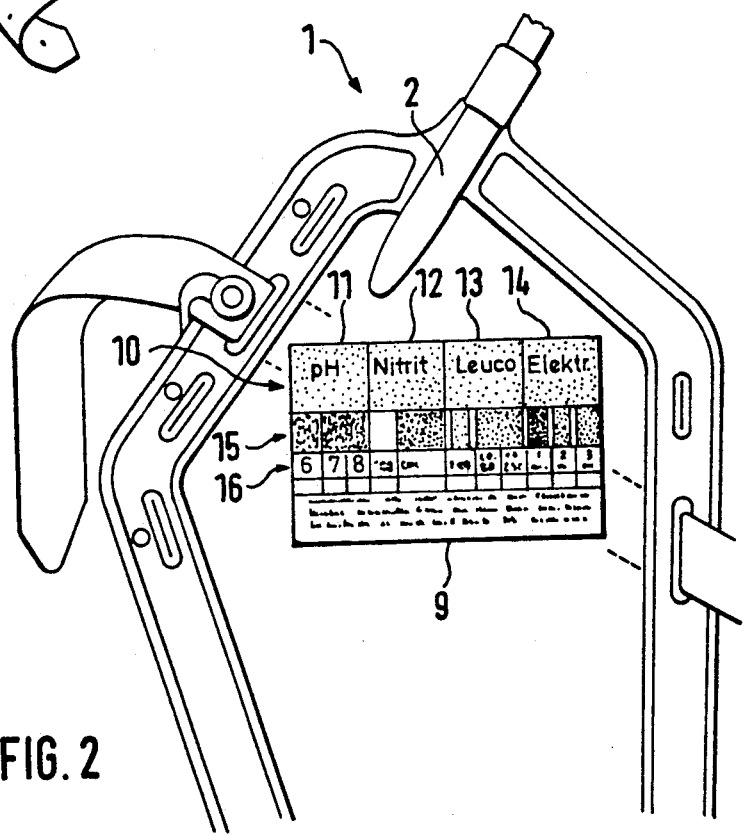
FIG. 2 shows a portion of the device according to FIG. 1 with a control card on the inside walling of the collecting bag, according to the invention.

FIG. 2 shows, of device 1 as in FIG. 1, a front view of inside walling 8 of collecting bag 3, to which a control card 9 is glued before bonding. Control card 9 has at the top an indicator field 10 having various indicator sections 11 to 14 whose indicators respond to pH, nitrite, leukocyte and electrolyte values. The indicators are at first white; when later exposed to the urine they can form colors In an acidic medium, section 11 of the pH value indicator will turn yellow and in an alkaline medium it Will turn blue. The other indicator sections 12 to 14 can also assume different colors, so that sections 11 to 14 show not only a qualitative indication but also a quantitative indication.

Under indicator field 10, control card 9 is printed with a color field 15 showing under each indicator section 11 to 14 several colors that the indicator thereabove can also assume.

In a third line under color field 15 there is an explanatory key field 16. The wearer of the device goes by the quantizing statement of each indicator section 11 to 14, above which the color is the same in the two upper lines.

Figure 3:
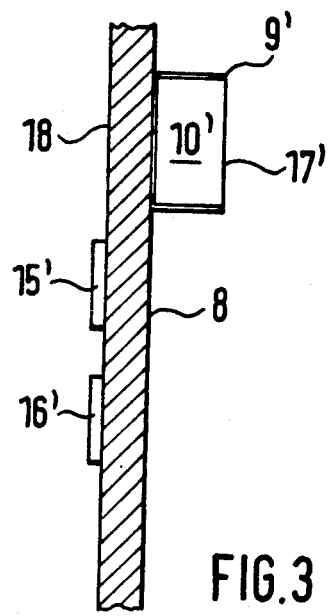
FIG. 3 shows a cross-section through a portion of the walling of a collecting bag of the type shown in FIG. 2 with a simplified control card compared to that in FIG. 2.

Indicator field 10' is covered on the urine-exposed side facing away from inside walling 8 with a membrane 17', as apparent in FIG. 3, that has a perforation formed by very small holes. Membrane 17' lets the urine penetrate to indicator field 10' only slowly. This prevents first urine with a high concentration of germs from causing, when it enters empty collecting bag 3, a supercritical indication that can normally not be triggered by midstream urine. The residual urine differing from the midstream can likewise not determine the indication alone; the urine instead hits indicator field 10' well mixed as a result of the slow passage through membrane 17'.

The indicator substances of indicator field 10 are embedded in a material that swells when exposed to moisture, so that when it swells it causes a pressure build-up against membrane 17' thereby impeding the passage of urine. This works against the color-forming indicator substances being washed out, and the indication values can still be read unfalsified after many hours.

Control card 9' shown in cross section in FIG. 3 consists only of an indicator field 10', which is identical to that in FIG. 2. Color field 15' and explanatory key field 16' for control card 9' are printed onto collecting bag 3 at a suitable place, preferably on its outside walling 18.

Figure 4:
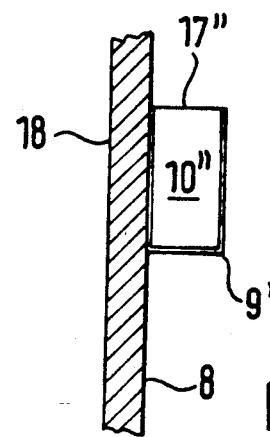
FIG. 4 shows a cross-section as in FIG. 3 but with a modified membrane assembly.

Control card 9" shown in FIG. 4 is sealed on the side of indicator field 10" facing away from inside walling 8. Membrane 17" responsible for the passage of urine extends along the narrow side of control card 9". The greatly reduced membrane area results in an accordingly slow passage of urine.

Perforated membrane 17" may be replaced by a semipermeable membrane.

Figure 5:
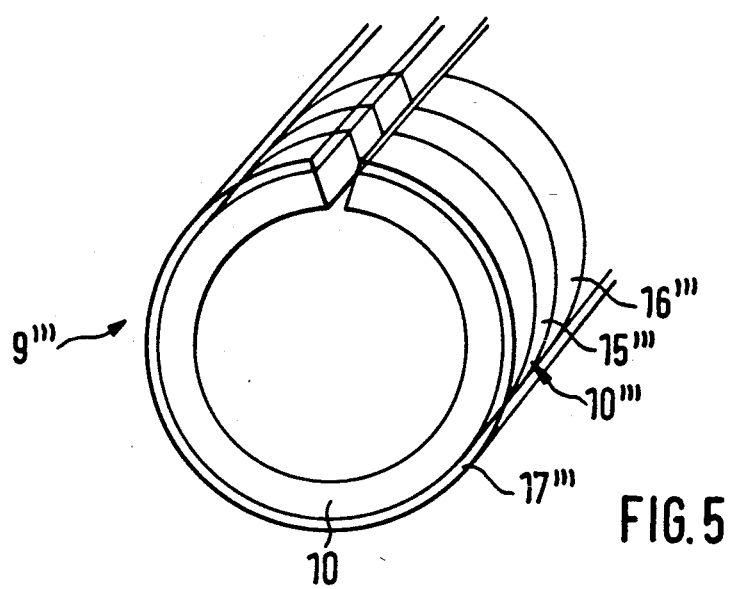
FIG. 5 shows a portion of a rolled-up control card.

FIG. 5 shows a rolled up control card 9''' that otherwise functions in the same way as above-described control cards 9, 9' and 9". In this embodiment the pressure increase is particularly pronounced due to the described swelling process.

The control card 9''' is rolled into a cylindrical shape; the membrane 17''' covers the outer surface of the cylinder and thereby retains the control card in its cylindrical shape. Because the control card is made of an absorptive material that swells after absorbing moisture, it impedes the diffusion of urine through the membrane.

The control card according to the present invention can also be made of a material that crystallizes after absorbing moisture. Furthermore, the idicators can include a substance that terminates the diffusion of urine by physical or chemical reaction. Finally, the membrane can be designed to control the diffusion of urine by effecting a structural change of the membrane during the diffusion process.

There has thus been shown and described a novel device for collecting uncontrollably released urine which fulfills all the objects and advantages sought therefor. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

I claim:

1. An incontinent urine collection device comprising (1) an introducing tube having means for connection to a body for receiving uncontrollably released urine therefrom; (2) a flexible, transparent urine-collecting bag connected to the tube to receive urine therefrom; (3) indicator means disposed in said bag for exposure to urine and having indicator substances to measure various values indicative of impending or existing germinal infections, said indicator means being disposed on a surface of a card disposed in said bag; and (4) means for diffusing urine to the indicator means slowly so that the urine passed represents a mixture of first, midstream and residual urine, but preventing the diffusion of the indicator substances from the card so that the indicator means values can be read accurately, said urine passing means comprising a membrane mounted on the surface of the card.

2. The device of claim 1, wherein the membrane has perforations consisting of very small holes.

3. The device of claim 1, wherein the membrane is made of a semipermeable material.

4. The device of claim 1, wherein the collection device further includes a comparative color field to assist a user in reading the indicator substances.

5. The device of claim 4, wherein an explanatory key field is associated with the comparative color field.

6. The device of claim 5, wherein the comparative color and explanatory key fields are printed on the outside of said bag.

7. The device of claim 1, wherein the card is rolled into a cylindrical shape and the membrane means includes means for retaining the card in said cylindrical shape.

8. The device of claim 1, wherein the card has a cylindrical shape and the membrane means covers the outer surface of the cylindrically-shaped card.

* * * * *